US009050005B2

(12) United States Patent
Ignagni et al.

(10) Patent No.: US 9,050,005 B2
(45) Date of Patent: Jun. 9, 2015

(54) METHOD AND APPARATUS FOR TRANSGASTRIC NEUROSTIMULATION

(75) Inventors: Anthony R. Ignagni, Oberlin, OH (US); Raymond P. Onders, Shaker Heights, OH (US); James E. Gelbke, North Royalton, OH (US)

(73) Assignee: Synapse Biomedical, Inc., Oberlin, OH (US)

( * ) Notice: Subject to any disclaimer, the term of this patent is extended or adjusted under 35 U.S.C. 154(b) by 533 days.

(21) Appl. No.: 11/467,014

(22) Filed: Aug. 24, 2006

(65) Prior Publication Data

US 2007/0049793 A1 Mar. 1, 2007

Related U.S. Application Data (60) Provisional application No. 60/596,029, filed on Aug. 25, 2005.

(51) Int. Cl.
*A61B 1/05* (2006.01)
*A61B 5/04* (2006.01)
*A61B 5/00* (2006.01)
*A61B 5/0488* (2006.01)
(Continued)

(52) U.S. Cl.
CPC ......... *A61B 5/04001* (2013.01); *A61B 5/04884* (2013.01); *A61B 1/273* (2013.01); *A61B 1/313* (2013.01); *A61B 5/0488* (2013.01); *A61B 5/4238* (2013.01); *A61N 1/36007* (2013.01)

(58) Field of Classification Search
USPC .................................. 606/14, 32; 607/42, 48
See application file for complete search history.

(56) References Cited

U.S. PATENT DOCUMENTS

| 1,693,734 A | 12/1928 | Waggoner |
| 2,532,788 A | 12/1950 | Sarnoff |

(Continued)

FOREIGN PATENT DOCUMENTS

| EP | 996482 A1 | 5/2000 |
| EP | 873155 B1 | 6/2003 |

(Continued)

OTHER PUBLICATIONS

Onders, Raymond P. "Mapping the phrenic nerve motor: the key to a successful laparoscopic diaphragm pacing system in the first human series." Surgery 136.4 (2004): 819-826. Web. Feb. 16, 2010.*

(Continued)

*Primary Examiner* — Jaymi Della
(74) *Attorney, Agent, or Firm* — Shay Glenn LLP (57) ABSTRACT

A method of placing an electrode in a peritoneal cavity including the following steps: inserting an endoscope through a patient's mouth into the patient's stomach; passing the endoscope through an opening in the stomach into the peritoneal cavity; and using the endoscope to place the electrode in contact with tissue within the peritoneal cavity other than stomach tissue. Another aspect of the invention provides a method of electrically mapping tissue accessed from a peritoneal cavity including the following steps: inserting an endoscope through a patient's mouth into the patient's stomach; passing the endoscope through an opening in the stomach into the peritoneal cavity; passing an electrode through the endoscope; placing the electrode in contact with tissue within the peritoneal cavity other than stomach tissue; and applying a mapping stimulation signal to the electrode from a mapping stimulator.

15 Claims, 6 Drawing Sheets

(51) Int. Cl.
*A61B 1/273* (2006.01)
*A61B 1/313* (2006.01)
*A61N 1/36* (2006.01)

(56) References Cited

U.S. PATENT DOCUMENTS

| | | | |
|---|---|---|---|
| 2,664,880 A | 1/1954 | Wales, Jr. | |
| 4,699,875 A | 10/1987 | Appel | |
| 4,773,393 A * | 9/1988 | Haber et al. | 600/30 |
| 4,827,935 A | 5/1989 | Geddes et al. | |
| 4,830,008 A | 5/1989 | Meer | |
| 4,863,438 A * | 9/1989 | Gauderer et al. | 604/247 |
| 4,989,617 A | 2/1991 | Memberg et al. | |
| 5,056,519 A | 10/1991 | Vince | |
| 5,074,846 A * | 12/1991 | Clegg et al. | 604/164.1 |
| 5,146,918 A | 9/1992 | Kallok et al. | |
| 5,314,463 A | 5/1994 | Camps et al. | |
| 5,335,657 A | 8/1994 | Terry et al. | |
| 5,368,035 A | 11/1994 | Hamm et al. | |
| 5,429,636 A * | 7/1995 | Shikhman et al. | 606/41 |
| 5,472,438 A | 12/1995 | Schmit et al. | |
| 5,483,969 A | 1/1996 | Testerman et al. | |
| 5,524,632 A | 6/1996 | Stein et al. | |
| 5,527,358 A | 6/1996 | Mehmanesh et al. | |
| 5,678,535 A | 10/1997 | DiMarco | |
| 5,716,392 A | 2/1998 | Bourgeois et al. | |
| 5,718,248 A | 2/1998 | Trumble et al. | |
| 5,792,165 A | 8/1998 | Klieman et al. | |
| 5,797,923 A | 8/1998 | Aiyar et al. | |
| 5,813,399 A | 9/1998 | Isaza et al. | |
| 5,814,086 A | 9/1998 | Hirschberg et al. | |
| 5,849,290 A | 12/1998 | Brown et al. | |
| 5,851,783 A | 12/1998 | Appel et al. | |
| 6,035,856 A | 3/2000 | LaFontaine et al. | |
| 6,194,217 B1 | 2/2001 | Matson | |
| 6,198,970 B1 | 3/2001 | Freed et al. | |
| 6,210,970 B1 | 4/2001 | Matson | |
| 6,245,053 B1 | 6/2001 | Benjamin | |
| 6,254,425 B1 | 7/2001 | Shchervinsky et al. | |
| 6,311,692 B1 | 11/2001 | Vaska et al. | |
| 6,321,109 B2 | 11/2001 | Ben-Haim et al. | |
| 6,360,740 B1 | 3/2002 | Ward et al. | |
| 6,397,108 B1 | 5/2002 | Camps et al. | |
| 6,405,732 B1 * | 6/2002 | Edwards et al. | 128/898 |
| 6,415,183 B1 | 7/2002 | Scheiner et al. | |
| 6,463,327 B1 | 10/2002 | Lurie et al. | |
| 6,477,423 B1 * | 11/2002 | Jenkins | 607/40 |
| 6,571,127 B1 | 5/2003 | Ben-Haim et al. | |
| 6,645,145 B1 | 11/2003 | Dreschel et al. | |
| 6,845,271 B2 | 1/2005 | Fang et al. | |
| 6,918,871 B2 | 7/2005 | Schulze | |
| 6,947,792 B2 | 9/2005 | Ben-Haim et al. | |
| 7,006,871 B1 | 2/2006 | Darvish et al. | |
| 7,044,921 B2 | 5/2006 | Asmus et al. | |
| 7,071,194 B2 | 7/2006 | Teng | |
| 7,107,092 B2 | 9/2006 | Goldstein et al. | |
| 7,120,497 B2 | 10/2006 | Ben-Haim et al. | |
| 7,155,278 B2 | 12/2006 | King et al. | |
| 7,165,551 B2 | 1/2007 | Edwards et al. | |
| 7,195,881 B2 | 3/2007 | Geffard | |
| 7,206,636 B1 | 4/2007 | Turcott | |
| 7,207,946 B2 | 4/2007 | Sirokman | |
| 7,221,978 B2 | 5/2007 | Ben-Haim et al. | |
| 7,225,016 B1 | 5/2007 | Koh | |
| 7,329,489 B2 | 2/2008 | Kaddurah-Daouk et al. | |
| 7,356,521 B2 | 4/2008 | Wang et al. | |
| 7,418,298 B2 | 8/2008 | Shiroff et al. | |
| 7,463,934 B2 | 12/2008 | Tronnes et al. | |
| 2001/0025177 A1 | 9/2001 | Woloszko et al. | |
| 2001/0049497 A1 | 12/2001 | Kalloo et al. | |
| 2002/0103424 A1 | 8/2002 | Swoyer et al. | |
| 2003/0040785 A1 | 2/2003 | Maschino et al. | |
| 2003/0148404 A1 | 8/2003 | Michaelson | |
| 2003/0171672 A1 | 9/2003 | Varghese et al. | |
| 2003/0175832 A1 | 9/2003 | Marton et al. | |
| 2004/0003813 A1 | 1/2004 | Banner et al. | |
| 2004/0044377 A1 | 3/2004 | Larsson | |
| 2004/0064069 A1 | 4/2004 | Reynolds et al. | |
| 2004/0122360 A1 | 6/2004 | Waldhauser et al. | |
| 2004/0127954 A1 | 7/2004 | McDonald | |
| 2004/0167437 A1 | 8/2004 | Sharrow et al. | |
| 2004/0167442 A1 | 8/2004 | Shireman et al. | |
| 2004/0167443 A1 | 8/2004 | Shireman et al. | |
| 2004/0172090 A1 | 9/2004 | Janzig et al. | |
| 2004/0177388 A1 | 9/2004 | Botas et al. | |
| 2004/0254572 A1 | 12/2004 | McIntyre et al. | |
| 2004/0260198 A1 | 12/2004 | Rothberg et al. | |
| 2004/0260245 A1 | 12/2004 | Clem et al. | |
| 2004/0260246 A1 | 12/2004 | Desmond | |
| 2004/0260337 A1 | 12/2004 | Freed | |
| 2005/0021102 A1 | 1/2005 | Ignagni et al. | |
| 2005/0033394 A1 | 2/2005 | Seifert et al. | |
| 2005/0042589 A1 | 2/2005 | Hatlestad et al. | |
| 2005/0049523 A1 | 3/2005 | Crank | |
| 2005/0054950 A1 | 3/2005 | Parins | |
| 2005/0054951 A1 | 3/2005 | Parins | |
| 2005/0054952 A1 | 3/2005 | Eskuri et al. | |
| 2005/0080463 A1 | 4/2005 | Stahmann et al. | |
| 2005/0085734 A1 | 4/2005 | Tehrani | |
| 2005/0085865 A1 | 4/2005 | Tehrani | |
| 2005/0085866 A1 | 4/2005 | Tehrani | |
| 2005/0085867 A1 | 4/2005 | Tehrani et al. | |
| 2005/0085868 A1 | 4/2005 | Tehrani et al. | |
| 2005/0085869 A1 | 4/2005 | Tehrani et al. | |
| 2005/0107781 A1 | 5/2005 | Ostrovsky et al. | |
| 2005/0107812 A1 | 5/2005 | Starksen et al. | |
| 2005/0107860 A1 | 5/2005 | Ignagni et al. | |
| 2005/0109340 A1 | 5/2005 | Tehrani | |
| 2005/0113710 A1 | 5/2005 | Stahmann et al. | |
| 2005/0115561 A1 | 6/2005 | Stahmann et al. | |
| 2005/0124917 A1 | 6/2005 | Skujins et al. | |
| 2005/0137501 A1 | 6/2005 | Euteneuer et al. | |
| 2005/0148026 A1 | 7/2005 | Bowser et al. | |
| 2005/0148818 A1 * | 7/2005 | Mesallum | 600/116 |
| 2005/0165457 A1 | 7/2005 | Benser et al. | |
| 2005/0209653 A1 * | 9/2005 | Herbert et al. | 607/40 |
| 2005/0240241 A1 | 10/2005 | Yun et al. | |
| 2005/0277945 A1 | 12/2005 | Saadat et al. | |
| 2006/0030894 A1 | 2/2006 | Tehrani | |
| 2006/0035849 A1 | 2/2006 | Spiegelman et al. | |
| 2006/0036294 A1 | 2/2006 | Tehrani | |
| 2006/0041022 A1 | 2/2006 | Pasinetti | |
| 2006/0068452 A1 | 3/2006 | Goldknopf et al. | |
| 2006/0088862 A1 | 4/2006 | Lee | |
| 2006/0115854 A1 | 6/2006 | Goldknopf et al. | |
| 2006/0115855 A1 | 6/2006 | Goldknopf et al. | |
| 2006/0115856 A1 | 6/2006 | Goldknopf et al. | |
| 2006/0115867 A1 | 6/2006 | Goldknopf et al. | |
| 2006/0121619 A1 | 6/2006 | Bowser | |
| 2006/0122662 A1 | 6/2006 | Tehrani et al. | |
| 2006/0130161 A1 | 6/2006 | Genain | |
| 2006/0130833 A1 | 6/2006 | Younes | |
| 2006/0142815 A1 | 6/2006 | Tehrani et al. | |
| 2006/0149316 A1 | 7/2006 | DeVries et al. | |
| 2006/0149334 A1 | 7/2006 | Tehrani et al. | |
| 2006/0155222 A1 | 7/2006 | Sherman et al. | |
| 2006/0155341 A1 | 7/2006 | Tehrani et al. | |
| 2006/0160087 A1 | 7/2006 | McGrath et al. | |
| 2006/0167523 A1 | 7/2006 | Tehrani et al. | |
| 2006/0200004 A1 * | 9/2006 | Wilk | 600/207 |
| 2006/0224209 A1 | 10/2006 | Meyer | |
| 2006/0237023 A1 * | 10/2006 | Cox et al. | 128/898 |
| 2006/0247729 A1 | 11/2006 | Tehrani et al. | |
| 2006/0258667 A1 | 11/2006 | Teng | |
| 2006/0281809 A1 | 12/2006 | Miller et al. | |
| 2006/0282131 A1 | 12/2006 | Caparso et al. | |
| 2006/0286167 A1 | 12/2006 | Staunton et al. | |
| 2006/0287679 A1 | 12/2006 | Stone | |
| 2007/0016172 A1 * | 1/2007 | Charukhchian | 606/1 |
| 2007/0017809 A1 | 1/2007 | Goldknopf et al. | |
| 2007/0021421 A1 | 1/2007 | Hampton | |
| 2007/0021500 A1 | 1/2007 | Twyman et al. | |
| 2007/0021795 A1 | 1/2007 | Tehrani | |
| 2007/0038127 A1 | 2/2007 | Goldstein et al. | |

(56) References Cited

U.S. PATENT DOCUMENTS

| | | |
|---|---|---|
| 2007/0054852 A1 | 3/2007 | Lin et al. |
| 2007/0072943 A1 | 3/2007 | Miller et al. |
| 2007/0078099 A1 | 4/2007 | McLaurin |
| 2007/0087000 A1 | 4/2007 | Walsh et al. |
| 2007/0087314 A1 | 4/2007 | Gomo |
| 2007/0098812 A1 | 5/2007 | Feinstein et al. |
| 2007/0117772 A1 | 5/2007 | Bennett et al. |
| 2007/0118183 A1 | 5/2007 | Gelfand et al. |
| 2007/0122813 A1 | 5/2007 | Salomon et al. |
| 2007/0150006 A1 | 6/2007 | Libbus et al. |
| 2007/0150023 A1 | 6/2007 | Ignagni et al. |
| 2007/0172820 A1 | 7/2007 | Kaddurah-Daouk et al. |
| 2007/0191908 A1 | 8/2007 | Jacob et al. |
| 2007/0196780 A1 | 8/2007 | Ware et al. |
| 2007/0197932 A1 | 8/2007 | Feke et al. |
| 2007/0202515 A1 | 8/2007 | Hadlock et al. |
| 2007/0202537 A1 | 8/2007 | Lingappa et al. |
| 2007/0221224 A1 | 9/2007 | Pittman et al. |
| 2007/0225261 A1 | 9/2007 | Miller et al. |
| 2007/0240718 A1 | 10/2007 | Daly |
| 2007/0250162 A1 | 10/2007 | Royalty |
| 2007/0265611 A1 | 11/2007 | Ignagni et al. |
| 2007/0274992 A1 | 11/2007 | Michalovich et al. |
| 2007/0282388 A1 | 12/2007 | Sandyk |
| 2007/0292403 A1 | 12/2007 | Nivaggioli |
| 2007/0292410 A1 | 12/2007 | Cashman et al. |
| 2007/0298998 A1 | 12/2007 | Paige et al. |
| 2008/0003208 A1 | 1/2008 | Nivaggioli |
| 2008/0121231 A1 | 5/2008 | Sinderby et al. |
| 2013/0218231 A1 | 8/2013 | Ignagni et al. |
| 2013/0238053 A1 | 9/2013 | Ignagni et al. |

FOREIGN PATENT DOCUMENTS

| | | |
|---|---|---|
| EP | 1634617 A1 | 3/2006 |
| EP | 1653863 A2 | 5/2006 |
| EP | 1658020 A1 | 5/2006 |
| EP | 1660177 A1 | 5/2006 |
| EP | 1663370 A2 | 6/2006 |
| EP | 1667757 A2 | 6/2006 |
| EP | 1670611 A2 | 6/2006 |
| EP | 1684655 A2 | 8/2006 |
| EP | 1393773 B1 | 10/2006 |
| EP | 1306104 B1 | 1/2007 |
| EP | 1205202 B1 | 6/2007 |
| WO | WO 86/00234 A1 | 1/1986 |
| WO | WO 2005/039691 A1 | 5/2005 |
| WO | WO 2005/044079 | 5/2005 |
| WO | WO 2006/062710 A1 | 6/2006 |
| WO | WO 2006/079152 A1 | 8/2006 |
| WO | WO 2006/083675 A2 | 8/2006 |
| WO | WO 2006/088696 A2 | 8/2006 |
| WO | WO 2006/121447 A2 | 11/2006 |
| WO | WO 2006/124023 A1 | 11/2006 |
| WO | WO 2006/131150 A1 | 12/2006 |
| WO | WO 2006/138069 A1 | 12/2006 |
| WO | WO 2007/035804 A2 | 3/2007 |
| WO | WO 2007/053230 A2 | 5/2007 |
| WO | WO 2007/058780 A2 | 5/2007 |
| WO | WO 2007/058938 A2 | 5/2007 |
| WO | WO 2007/061902 A2 | 5/2007 |
| WO | WO 2007/082384 A1 | 7/2007 |
| WO | WO 2007/103585 A2 | 9/2007 |
| WO | WO 2007/109443 A2 | 9/2007 |
| WO | WO 2007/128002 A2 | 11/2007 |

OTHER PUBLICATIONS

D'Honneur, G., V. Slavov, et al. "Comparison of the effects of mivacurium on the diaphragm and geniohyoid muscles." British Journal of Anesthesia. 77. (1996): 716-719.*

Ayas et al; Prevention of human diaphragm atrophy with short periods of electrical stimulation; Am J Respir Crit Care Med; vol. 159; pp. 2018-2020; 1999.

DiMarco et al.; Phrenic nerve pacing in a tetraplegic patient via intramuscular diaphragm electrodes; American Journal of Respiratory and Critical Care Medicine; vol. 166 (12 Pt 1); pp. 1604-1606; Dec. 15, 2002.

DiMarco A. F.; Restoration of respiratory muscle function following spinal cord injury—Review of electrical and magnetic stimulation techniques; Respiratory Physiology & Neurobiology; 147; 273-287; 2005.

Knutson et al.; Electrode fracture rates and occurrences of infection and granuloma associated with percutaneous intramuscular electrodes in upper-limb functional electrical stimulation applications; Journal of Rehabilitation Research and Development; vol. 39; No. 6; pp. 671-684, Nov./Dec. 2002.

Nochomovitz et al.; Conditioning of the diaphragm with phrenic nerve stimulation after prolonged disuse; American Review of Respiratory Disease; vol. 130; No. 4; 325-329; Oct. 1984.

Nochomovitz et al.; Diaphragm activation with intramuscular stimulation in dogs; American Review of Respiratory Disease; vol. 127; No. 3; 685-687; Mar. 1983.

Onders et al.; Mapping the phrenic nerve motor point: the key to a successful laparoscopic diaphragm pacing system in the first human series; Surgery; vol. 136; No. 4; 819-26; Oct. 2004.

Peterson et al.; Long-term intramuscular electrical activation of the phrenic nerve: Safety and reliability; IEEE; vol. 41; No. 12; pp. 1115-1126; Dec. 1994.

Peterson et al.; Electrical activation of respiratory muscles by methods other than phrenic nerve cuff electrodes; Pacing and Clinical Electrophysiology; vol. 12; No. 5; pp. 854-878; May 1989.

Peterson et al.; Intramuscular electrical activation of the phrenic nerve; IEEE Transactions on Biomedical Engineering; vol. BME-33; No. 3; 342-351; Mar. 1986.

Polkey et al.; Influence of acute lung volume change on contractile properties of human diaphragm; Journal of Applied Physiology; vol. 85, No. 4; pp. 1322-1328; Oct. 1998.

Sarnoff et al.; Electrophrenic respiration; Science; vol. 108; 482; Oct. 29, 1948.

Schmit, et al.; Laparoscopic placement of electrodes for diaphragm pacing using stimulation to locate the phrenic nerve motor points; IEEE Trans on Rehab Engineer; vol. 6; No. 4; 382-390; Dec. 1998.

Ignagni et al; U.S. Appl. No. 11/716,475 entitled "Ventilatory assist system and methods to improve respiratory function," filed Mar. 9, 2007.

Ignagni et al; U.S. Appl. No. 11/467,025 entitled "Method and apparatus for grasping an abdominal wall," filed Aug. 24, 2006.

Ignagni et al; U.S. Appl. No. 12/026,428 entitled "Intramuscular electrode," filed Feb. 5, 2008.

Ignagni et al.; U.S. Appl. No. 12/261,979 entitled "Method of improving sleep disordered breathing," filed Oct. 30, 2008.

Onders et al.; U.S. Appl. No. 12/122,482 entitled "Devices and methods for assessing motor point electromyogram as a biomarker," filed May 16, 2008.

DeCarvalho et al.; Motor neuron disease presenting with respiratory failure; Journal of the Neurological Sciences; vol. 139; No. Suppl.; 1996; pp. 117-122.

Stewart et al.; Electromyography of respiratory muscles in amyotrophic lateral sclerosis; Journal of the Neurological Sciences; vol. 191; No. 1-2; Oct. 15, 2001; pp. 67-73.

Ignagni et al.; U.S. Appl. No. 12/904,993 entitled "System and Method for Conditioning a Diaphragm of a Patient," filed Oct. 14, 2010.

Bhadra et al.; Extraction force and tissue change during removal of a tined intramuscular electrode from rat gastrocnemius; Annals of Biomedical Engineering; vol. 34; No. 6; pp. 1042-1050; Jun. 2006.

Onders et al.; Early results of laparoscopic motor point diaphragm pacing in amyotrophic lateral sclerosis; Amyotrophic Lateral Scle-

(56) References Cited

OTHER PUBLICATIONS rosis (Abstracts from the 16th Intl. Symp. ALS/MND; vol. 6, supp. 1; ISSN1743-4475; pp. 142-143; Dec. 2005.

Zifko et al.; Central and peripheral respiratory electrophysiological studies in myotonic dystrophy; Brain; vol. 119; 1996; pp. 1911-1922.

Kalloo et al.; Flexible transgastric peritoneoscopy: a novel approach to diagnosis and therapeutic intervention in the peritoneal cavity; Gastrointestinal Endoscopy; vol. 60; No. 1; pp. 114-117; 2004.

Ignagni et al.; U.S. Appl. No. 12/690,410 entitled "Device and Method of Neuromodulation to Effect a Functionally Restorative Adaption of the Neuromuscular System," filed Jan. 20, 2010.

de Carvalho et al.; Medical technology assessment: Electrodiagnosis in motor neuron diseases and amyotrophic lateral sclerosis; Neurophysiol. Clin.; 31 (5); pp. 341-348; Oct. 2001.

McGee et al.; A reliable method for monitoring intraabdominal pressure during natural orifice translumenal endoscopic surgery; Surg Endosc.; 21(4): pp. 672-676; Apr. 2007.

Onders, Raymond P.; The Utility of Flexible Endoscopy During Advanced Laparoscopy; Seminars in Laparoscopic Surgery; vol. 10, No. 1; pp. 43-48; Mar. 2003.

\* cited by examiner

METHOD AND APPARATUS FOR TRANSGASTRIC NEUROSTIMULATION

CROSS-REFERENCE

This application claims the benefit of U.S. Provisional Application No. 60/596,029, filed Aug. 25, 2005, which is incorporated herein by reference in its entirety.

This application is related to the following patent application, filed on even date herewith: "Method And Apparatus For Grasping An Abdominal Wall," U.S. Patent Publication No. 2008/0097153, which is incorporated herein by reference in its entirety.

BACKGROUND OF THE INVENTION

Certain neurostimulation procedures require the placement of electrodes via abdominal access. For example, US Patent Appl. Publ. No. 2005/0021102 describes a system and method for stimulating a conditioning a diaphragm through electrical stimulation of target sites on the diaphragm. The electrodes may be implanted laparoscopically, using, e.g., an electrode delivery instruments such as those described in U.S. Pat. Nos. 5,797,923 and 5,472,438.

It is often desirable to electrically map possible stimulation electrode sites to find the most appropriate target site for implanting the stimulation electrode(s). An example of a mapping probe system for use with neuromuscular stimulation systems is described in US Patent Appl. Publ. No. 2005/0107860. This mapping probe is designed to be inserted laparoscopically through a cannula that has been placed in the patient's peritoneal cavity through an incision in the patient's abdominal wall.

While less invasive than open surgery, laparoscopic delivery of mapping and/or stimulation electrodes still requires the surgeon to make multiple incisions through the patient's skin to access to the patient's abdomen for the visualization and electrode manipulation instruments. In addition, access to certain sites within and around the abdomen may be difficult, depending on the location of the laparoscopic port with respect to the target sites. While transesophageal approaches to cardiovascular and mediastinal procedures have been proposed (see, e.g., US Patent Appl. Publ. No. 2005/0148818), and while transgastric peritoneal cavity access tools have been described (see, e.g., U.S. Pat. No. 6,918,871; US Patent Appl. Publ. No. 2004/0260245; US Patent Appl. Publ. No. 2005/0277945; and US Patent Appl. Publ. No. 2001/0049497), the prior art has not addressed transgastric neuromapping and neurostimulation procedures in the peritoneal cavity. What is needed, therefore, are methods and devices for delivering mapping and/or stimulation electrodes to their target sites in and around the abdomen. In particular, what is needed is a better way to removably deliver mapping electrodes to multiple tissue sites within and around the peritoneal cavity.

SUMMARY OF THE INVENTION

One aspect of the invention provides a method of placing an electrode in a peritoneal cavity including the following steps: inserting an endoscope through a patient's mouth into the patient's stomach; passing the endoscope through an opening in the stomach into the peritoneal cavity; and using the endoscope to place the electrode in contact with tissue within the peritoneal cavity other than stomach tissue. In some embodiments, the method also includes the step of using the electrode to map electrical activity in the tissue and may also include the step of passing a mapping instrument comprising the electrode through the endoscope before the step of using the endoscope to place the electrode. In some embodiments, the method includes the step of using the electrode to electrically stimulate the tissue.

In some embodiments, the using step includes the step of inserting the electrode into the peritoneal cavity percutaneously under visualization from the endoscope and may also include the step of grabbing the electrode with an instrument associated with the endoscope. In some embodiments, the inserting step includes the step of inserting the electrode at an insertion site in an abdominal wall, the method further including the step of pulling the abdominal wall away from the stomach.

In some embodiments, the using step comprises includes the step of inserting the electrode into the peritoneal cavity laparoscopically under visualization from the endoscope and may also include the step of grabbing the electrode with an instrument associated with the endoscope. In some embodiments, the using step includes the step of inserting the electrode through the endoscope.

Another aspect of the invention provides a method of stimulating target tissue in or near a peritoneal cavity including the following steps: inserting an endoscope through a patient's mouth into the patient's stomach; passing the endoscope through an opening in the stomach into the peritoneal cavity; using the endoscope to place a stimulation electrode in contact with target tissue within the peritoneal cavity other than stomach tissue; and providing a stimulation signal to the electrode. In some embodiments, the method also includes the step of electrically mapping the target tissue with a mapping electrode inserted through the endoscope before placing the stimulation electrode.

In some embodiments, the using step includes the step of inserting the stimulation electrode into the peritoneal cavity percutaneously under visualization from the endoscope and may include the step of grabbing the stimulation electrode with an instrument associated with the endoscope.

In some embodiments, the using step includes the step of inserting the stimulation electrode into the peritoneal cavity laparoscopically under visualization from the endoscope and may include the step of grabbing the stimulation electrode with an instrument associated with the endoscope. In some embodiments, the using step includes the step of inserting the stimulation electrode through the endoscope.

Yet another aspect of the invention provides a method of electrically mapping tissue accessed from an peritoneal cavity including the following steps: inserting an endoscope through a patient's mouth into the patient's stomach; passing the endoscope through an opening in the stomach into the peritoneal cavity; passing an electrode through the endoscope; placing the electrode in contact with tissue within the peritoneal cavity other than stomach tissue; and applying a mapping stimulation signal to the electrode from a mapping stimulator. In some embodiments, the method includes the step of identifying a target stimulation site after applying the mapping stimulation signal. In some embodiments, the method also includes the step of placing a stimulation electrode at the target stimulation site. In some embodiments, the placing step may be performed percutaneously, laparoscopically or by passing the electrode through the endoscope.

The invention is described in more detail below with reference to the drawings.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

One aspect of the invention provides devices and techniques for diagnostic and therapeutic stimulation of abdominal and pelvic structures accessed through natural orifices, such as the mouth. The technique uses a standard endoscope and instruments to make a gastrostomy. The endoscope may then be passed into the peritoneal space within the peritoneal cavity and manipulated (by, e.g., bending or retroflexing) to view desired structures. A mapping instrument may be passed through one of the endoscope working channels to diagnose or identify structures. Upon completion of mapping, stimulating electrodes may be placed into target tissue using a percutaneous needle under endoscopic visualization and assistance. Alternatively, electrodes may be passed through a lumen of the endoscope. The electrode leads then may be attached to a stimulator disposed within the patient (e.g., in a subcutaneous pocket formed in the patient) and or percutaneously to an external stimulator.

The devices and techniques according to this aspect of the invention may be applied to a wide variety of disorders of the abdomen and pelvis. In many of these procedures, the target location or site is mapped prior to placement of either a trial percutaneous lead or a permanent implantable pulse generator.

Figure 1:
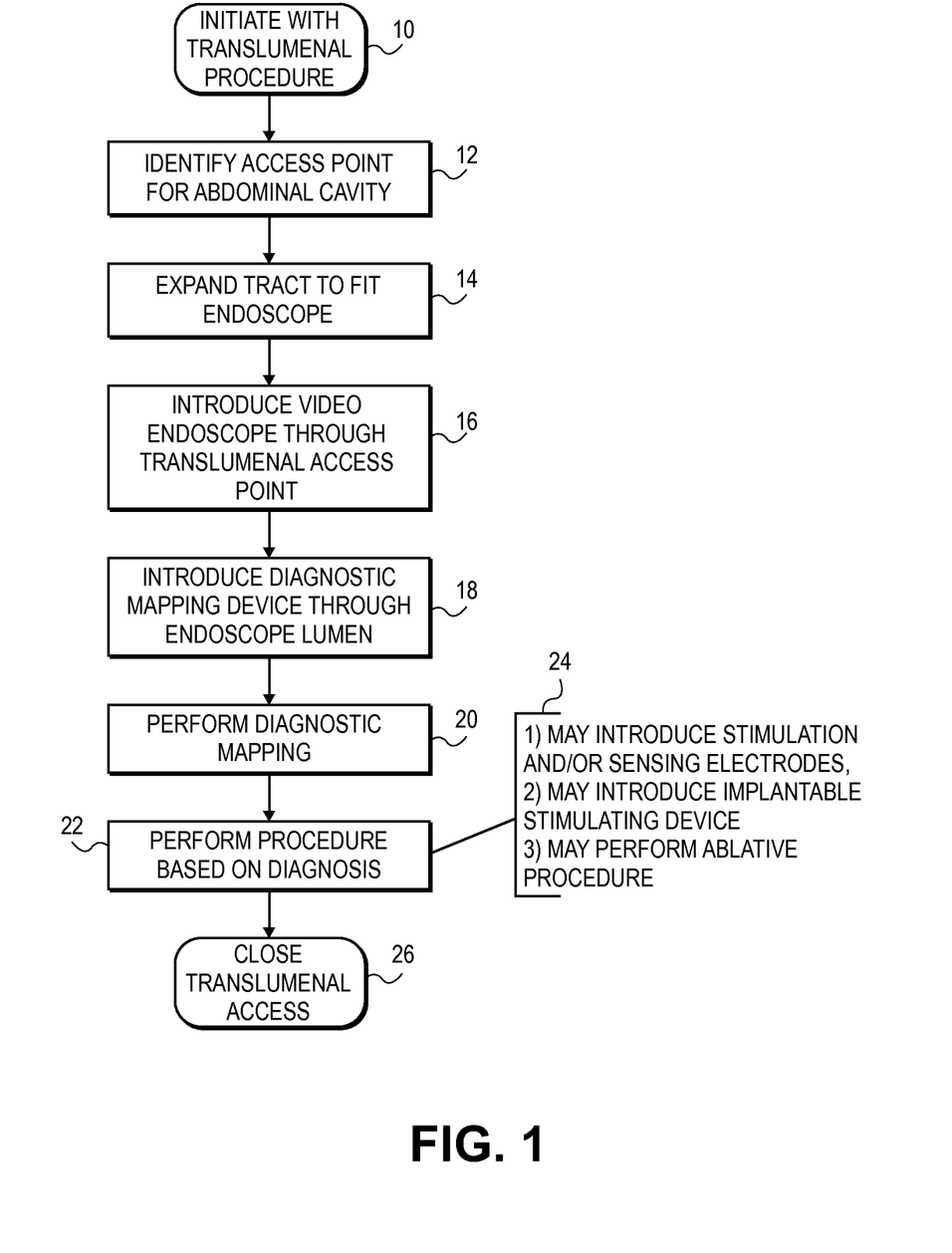
FIG. 1 is a flow chart showing an aspect of a tissue mapping method of this invention.

FIG. 1 is a flow chart showing an aspect of a tissue mapping method of this invention. The procedure initiates by placing an endoscope into the patient's stomach to provide translumenal access to the stomach wall, as in block 10 in FIG. 1. Using the endoscope's viewing capabilities, a peritoneal cavity access point in the stomach wall is identified (12). For example, one desirable section of stomach for this procedure may be located as far distally as is accessible by the endoscope, in a location that provides good visualization of the target abdominal or pelvic structures and that permits ready closing with a closing device.

After an opening is made in the stomach wall using a standard technique (e.g., gastrostomy), the opening is expanded to accommodate the endoscope (14), and the distal end of the endoscope is passed through the opening into the peritoneal cavity (16). After using the endoscope's viewing capabilities to locate target tissue site, a diagnostic mapping device is passed through a lumen of the endoscope so that its distal end is in the peritoneal cavity (18). Diagnostic electrical mapping may be then be performed on the target tissue (20). The mapping procedure may be used to diagnose the patient and to determine which therapeutic procedure should be performed, such as the implantation of stimulation or sensing electrodes, implantation of a stimulating device and/or tissue ablation (22, 24).

After completion of the procedure, the opening in the stomach is closed, and the endoscope is removed from the patient (26). Gastrostomy closing may be performed by placement of a percutaneous endoscopic gastrostomy (PEG) tube or by use of a ligating system, clip or T-bar device cinched to close the opening without placement of a PEG.

Figure 2:
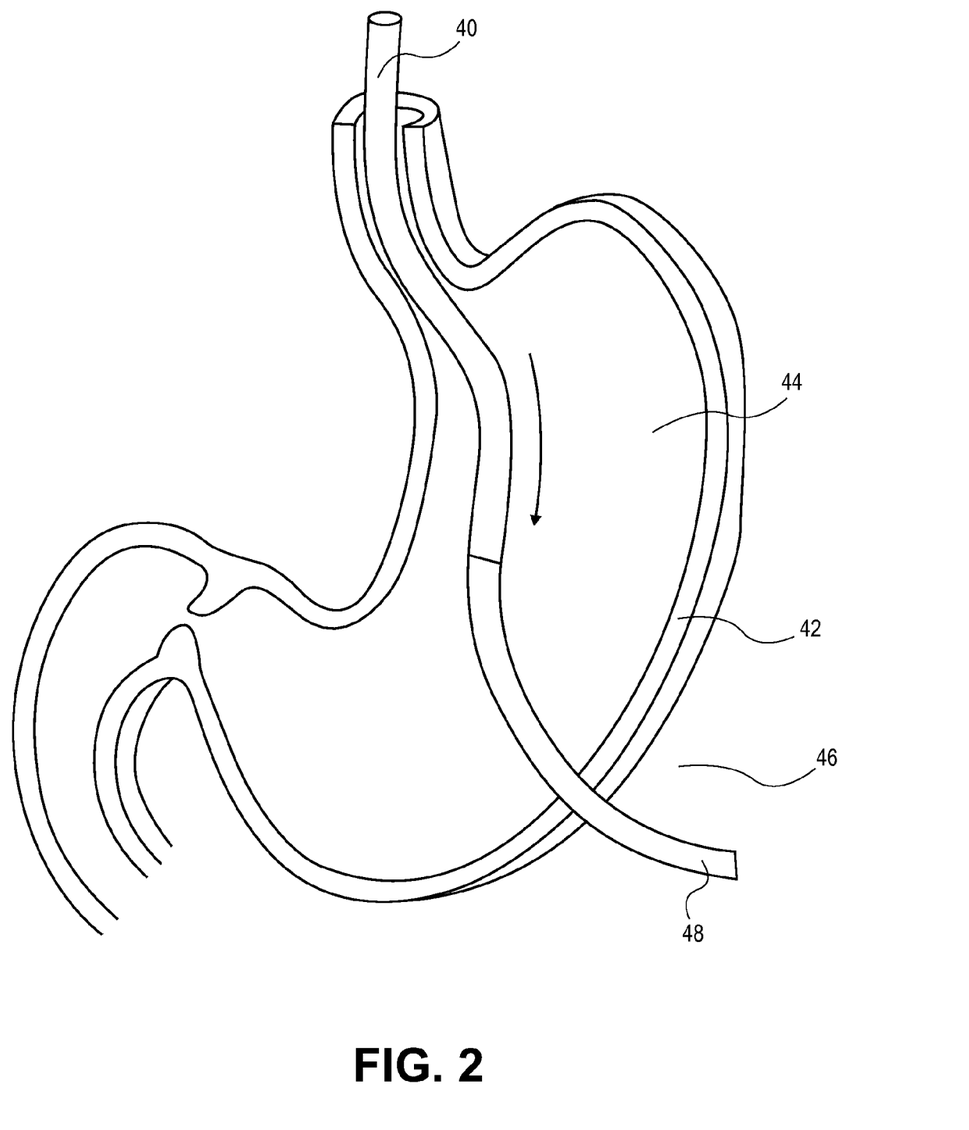
FIG. 2 shows an endoscope passing into a peritoneal cavity through an opening in a stomach.
Figure 3:
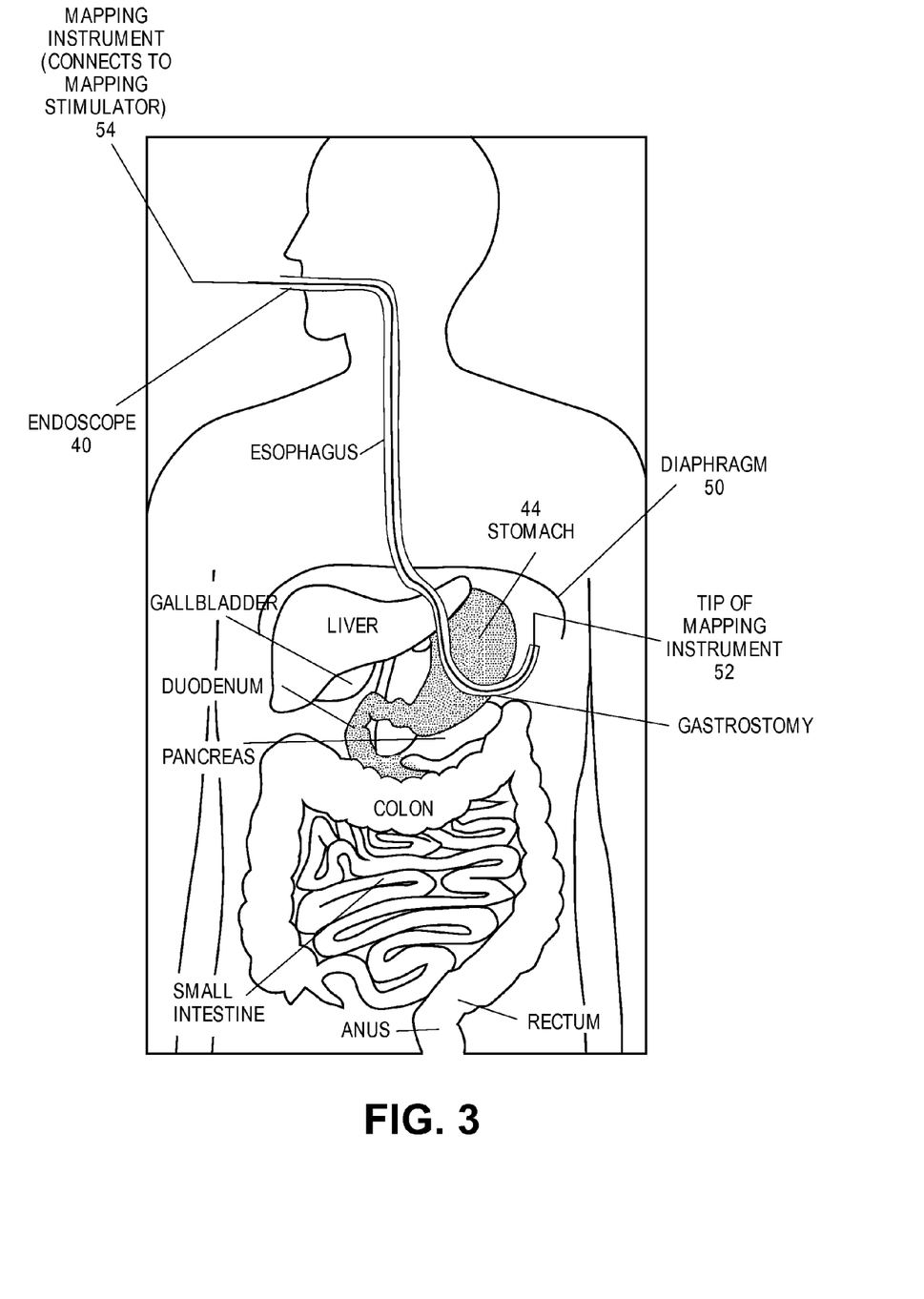
FIG. 3 show an endoscope and mapping instrument passing into a peritoneal cavity through an opening in a stomach and retroflexed toward a diaphragm.
Figure 4:
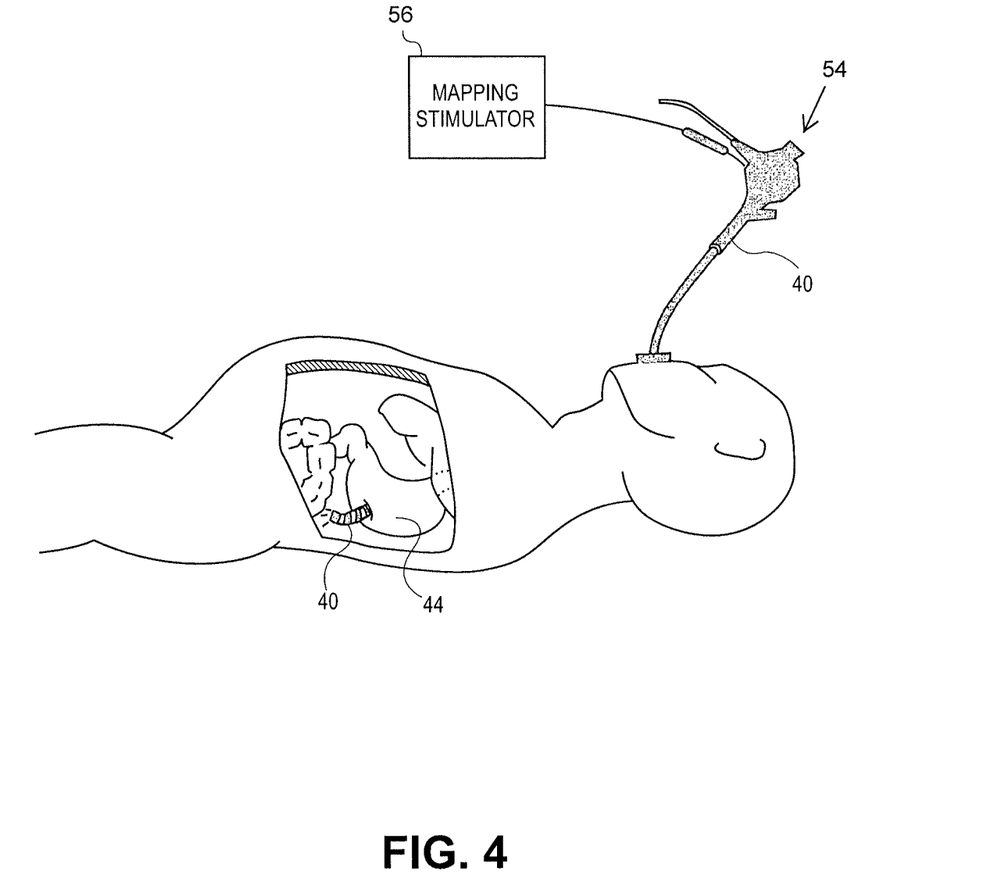
FIG. 4 shows an endoscope and mapping instrument passing into a peritoneal cavity through an opening in a stomach.

FIGS. 2-4 show an endoscope 40 passing into and through the wall 42 of a stomach 44 into the peritoneal cavity 46. The distal end 48 of the endoscope 40 may be retroflexed to view and/or provide access to, e.g., the patient's diaphragm 50, as shown in FIG. 3, which shows a mapping electrode 52 at the tip of a mapping instrument near the diaphragm. Other organs within and around the peritoneal cavity may be accessed, as shown. FIG. 4 shows how an external mapping stimulator 56 may be connected with a mapping instrument 54. Other details regarding the formation of a gastrostomy, endoscopic access to the peritoneal cavity through a gastrostomy, and tissue mapping and stimulation in general may be found in U.S. Pat. No. 6,918,871; US Patent Appl. Publ. No. 2004/0260245; US Patent Appl. Publ. No. 2005/0277945; US Patent Appl. Publ. No. 2001/0049497; US Patent Appl. Publ. No. 2005/0021102; and US Patent Appl. Publ. No. 2005/0107860.

Figure 5:
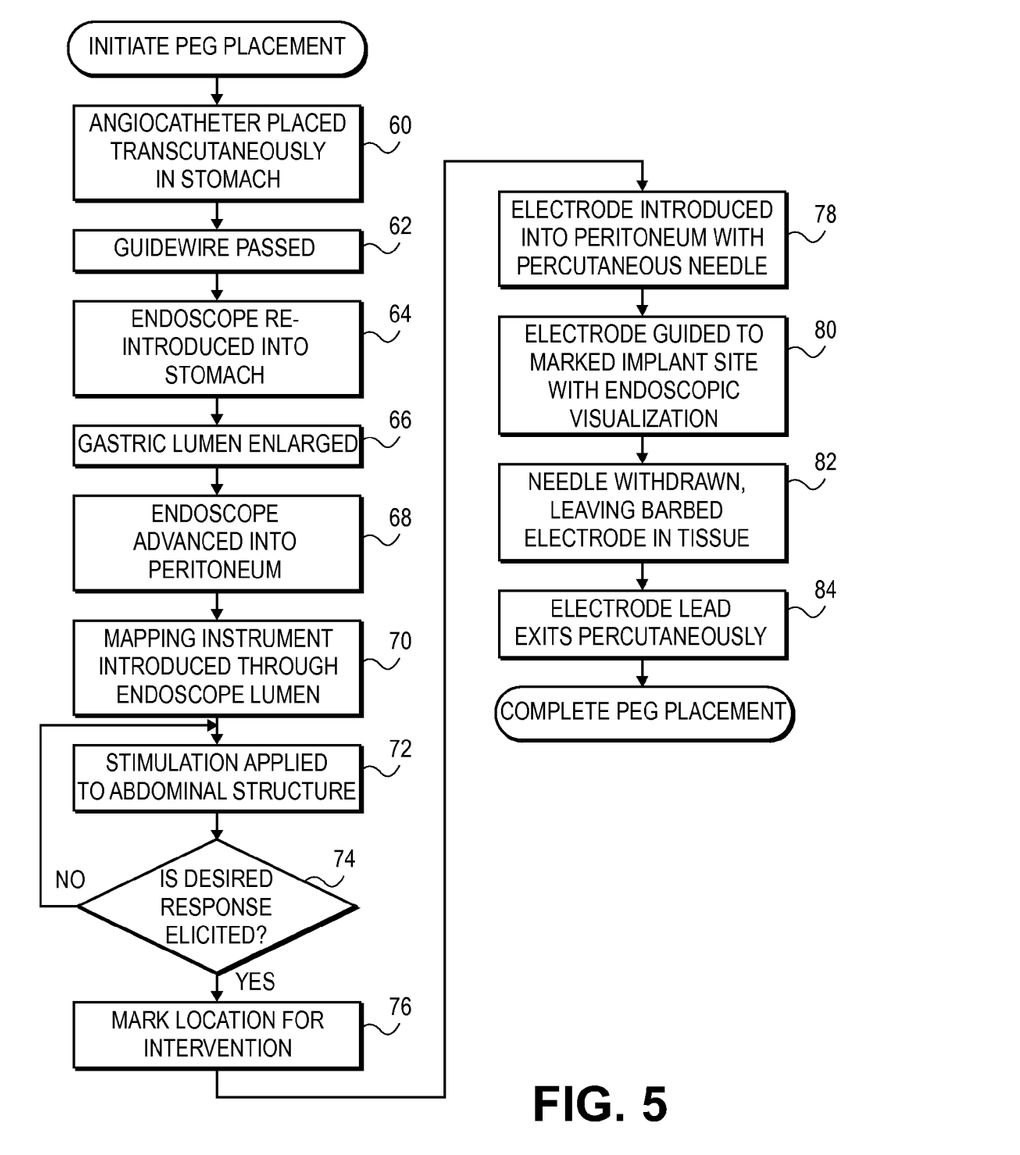
FIG. 5 is a flowchart showing another aspect of the transgastric mapping and electrode placement methods of this invention.

FIG. 5 is a flowchart showing another aspect of the transgastric mapping and electrode placement methods of this invention. A percutaneous endoscopic gastrostomy procedure commences by placing an angiocatheter percutaneously in the patient's stomach (60). A guidewire is then passed into the stomach (62), and an endoscope is introduced (or re-introduced) into the stomach (64). The guidewire may be snared by the endoscope and pulled out of the patient's mouth, and a second guidewire may be introduced with the first guidewire to provide a guide for re-introduction of the endoscope. An overtube may also be provided with the endoscope upon re-introduction. The gastric lumen or opening formed by the angiocatheter placement is enlarged, such as with a dilating balloon passed down the guidewire (66), and the distal tip of the endoscope is advanced through the opening into the patient's peritoneum (surrounding the peritoneal cavity) (68). The second guidewire and dilating balloon may then be removed.

After movement of the endoscope (e.g., bending, retroflexing) for visualization of the target structures, a mapping instrument may be passed through a lumen of the endoscope to stimulate and map target tissue within the peritoneal cavity (70, 72). Mapping stimulation responses may be monitored with instrumentation (e.g., EMG, ENG, pressure catheters, etc.) or queried from the patient (as in the case of awake endoscopy for identifying source of chronic pain). The mapping stimulation may be a single pulse to evoke a twitch or action potential or a train of pulses to elicit a contraction or propagation of nervous system impulses. If the desired response is not elicited in the target tissue, the mapping stimulation may be repeated (74). Otherwise, if mapping is successful, the target site may be marked for electrode placement or other intervention (76).

A stimulation electrode may then introduced into the peritoneum and placed in the target tissue, such as by a percutaneous needle under visualization from the endoscope (78, 80, 82). For example, an electrode such as a barbed style electrode (e.g., a Synapse Peterson, Memberg or single helix electrode) may be loaded into a non-coring needle and penetrated through the skin. Using endoscopic visualization and (if desirable or necessary) with an endoscopic grasping tool, the electrode may be placed in the target tissue. The needle may then be removed, leaving the electrode leads extending percutaneously for connection to an external stimulation device (84). Alternatively, barbed electrodes may be placed endoscopically by introducing a small gauge needle through a lumen of the endoscope for direct placement in the target tissue. The electrode leads may be connected to a subcutaneously-placed stimulator or to a microstimulator (such as a BION® microstimulator) passed through the endoscope lumen and placed with the electrode. As yet another alternative, the electrode may be placed laparoscopically using a single laparoscopic port and visualization from the endoscope. This alternative may permit the manipulation and placement of larger electrodes in the peritoneal cavity.

Figure 6:
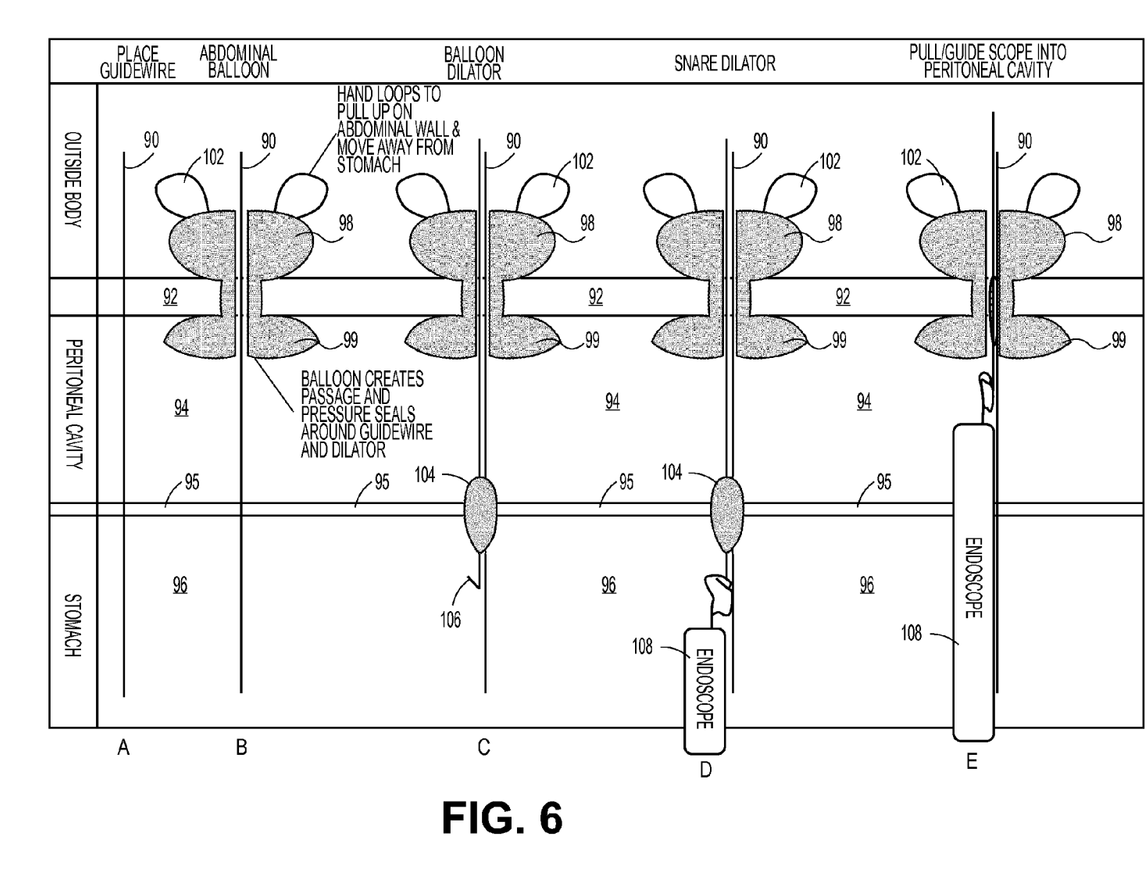
FIG. 6A-E are schematic drawings showing a transgastric procedure according to an aspect of this invention.

6A-E show schematically some of steps of endoscopic transgastric access of the peritoneal cavity according to one aspect of the invention. In FIG. 6A, a guidewire 90 is inserted percutaneously through the patient's abdominal wall 92, through the peritoneal cavity 94 and into the patient's stomach 96. A grasping device formed as a balloon 98 with a port 100 is placed around guidewire 90 and inflated to provide a pressure seal around the guidewire, as shown in FIG. 6B. An attachment portion 99 of balloon 98 extends through the abdominal wall 92, as shown, to firmly attach the grasping device to the abdominal wall. Balloon 98 has grasping elements formed as loops 102 that may be grasped by a user's fingers to pull the abdominal wall 92 away from the stomach during the procedure. A dilator 104 is advanced in a deflated configuration through the stomach wall 95 over guidewire 90, then inflated to enlarge the stomach wall opening, as shown in FIG. 6C. A snare 106 extending from dilator 104 grasps the distal end of endoscope 108 to pull endoscope 108 into the peritoneal cavity, as shown in FIGS. 6D and 6E. Use of the grasping loops 102 to pull the abdominal wall 92 away from stomach 96 is particularly useful during this portion of the procedure. Dilator 104 may be deflated, and snare 106 unhooked from endoscope 108, to permit endoscope 108 to be used in the peritoneal cavity as described above.

The devices and methods described above may be used as part of many procedures, such as:

Diaphragm conditioning. The device and method may be used to identify phrenic nerve motor points and to implant electrodes in the diaphragm to condition or pace the diaphragm.

Gastro-esophageal reflux disease (GERD) treatment. Mapping of structures within the peritoneal cavity may be used to identify a stimulus location to elicit the best contraction of the lower esophageal sphincter (LES). A trial electrode may then be placed in the LES, and a pH sensor placed in the esophagus. After two or three days of reduced reflux, the electrode may be connected to an implantable pulse generator (IPG).

Gastroparesis. Mapping may be used to identify a stimulus location that causes stomach wall contraction. A trial electrode placed in the stomach with the electrode lead passing percutaneously outside of the patient. Upon demonstration of improved gastric emptying and reduction in nausea, the electrode may be connected to an IPG.

Morbid obesity. Mapping may be used to elicit a sensation of satiety. Trial electrodes may be placed in the stomach with the electrode leads passing percutaneously outside of the patient. The electrodes may be removed after successful weight loss or connected to an IPG if on-going treatment is required.

Chronic pain from pancreatitis treated by neuromodulation at the celiac plexus. Mapping may be used to identify a location where neuromodulation of pain takes place, and trial electrode placed into the celiac plexus. Following a demonstration of pain reduction, the temporary lead or electrode may be connected to an IPG.

Chronic pain from unspecified abdominal or pelvic pain, treated by neuromodulation at the superior hypogastric plexus, the mesenteric plexus, or other nervous system structure through which the pain pathways are mediated. Mapping may be used to identify the location where neuromodulation of pain takes place. Following demonstrated trial pain reduction, the temporary lead or electrode may be connected in to an IPG.

Nerve sparing. The devices of this invention may be used diagnostically to identify specific tissue structures a surgeon may wish to spare during a surgical procedure. A mapping stimulus may be applied to nerve or muscle tissue to elicit a response, responsive tissue noted or marked, and marked tissue may be avoided during the subsequent surgical procedure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of transcutaneously implanting a stimulation electrode in a peritoneal cavity of a patient using transgastric mapping and guidance, the method comprising:
    inserting an endoscope having a proximal end and a distal end through a mouth into a stomach;
    passing the distal end of the endoscope through an opening in the stomach into the peritoneal cavity;
    retroflexing the distal end of the endoscope to orient the distal end of the endoscope towards a diaphragm, the retroflexed distal end of the endoscope configured to bend at least 90 degrees;
    inserting a mapping instrument having a mapping electrode through the endoscope and into the peritoneal cavity, the mapping instrument adapted to pass through the retroflexed endoscope;
    using the endoscope to place the mapping electrode in contact with the diaphragm of the patient within the peritoneal cavity;
    using the mapping electrode, coupled to a mapping stimulator, to map electrical activity in the diaphragm; and
    transcutaneously positioning a stimulation electrode using a percutaneous needle into the peritoneal cavity under visualization from the endoscope based on the mapped electrical activity in the diaphragm.

2. The method of claim 1 wherein the step of using the mapping electrode comprises using the mapping electrode to electrically stimulate the diaphragm.

3. The method of claim 1 further comprising grabbing the stimulation electrode with an instrument associated with the endoscope.

4. The method of claim 1 wherein the transcutaneously positioning step comprises inserting the stimulation electrode at an insertion site in an abdominal wall, the method further comprising pulling the abdominal wall away from the stomach.

5. The method of claim 1, wherein the percutaneous needle is non-coring.

6. A method of implanting a stimulation electrode transcutaneously using transgastric mapping and guidance for stimulating target tissue in or near a peritoneal cavity of a patient, the method comprising:
  inserting an endoscope through a mouth into a stomach;
  passing the endoscope through an opening in the stomach into the peritoneal cavity;
  laparoscopically placing a stimulation electrode at a target site on a diaphragm;
  using the endoscope to guide placement of the stimulation electrode based on a map of electrical activity in the diaphragm;
  closing the opening in the stomach by placement of a percutaneous endoscopic gastrostomy tube; and
  providing a stimulation signal to the stimulation electrode.

7. The method of claim 6 further comprising electrically mapping the diaphragm with a mapping electrode inserted through the endoscope before placing the stimulation electrode.

8. The method of claim 6 wherein the using step comprises inserting the stimulation electrode into the peritoneal cavity percutaneously under visualization from the endoscope.

9. The method of claim 8 further comprising grabbing the stimulation electrode with an instrument associated with the endoscope.

10. The method of claim 6 further comprising grabbing the stimulation electrode with an instrument associated with the endoscope.

11. A method of transcutaneously implanting a stimulation electrode in a diaphragm of a patient using transgastric mapping and guidance, the method comprising:
  inserting an endoscope through a mouth into a stomach;
  inserting a guidewire percutaneously through an abdominal wall, through a peritoneal cavity, through a stomach wall and into a stomach;
  inserting a dilator in a collapsed configuration over the guidewire and through the stomach wall;
  expanding the dilator to enlarge an opening in the stomach wall;
  passing the endoscope through the opening in the stomach wall into the peritoneal cavity;
  passing a mapping electrode through the endoscope;
  placing the mapping electrode in contact with a diaphragm of the patient within the peritoneal cavity; and
  applying a mapping stimulation signal to the mapping electrode from a mapping stimulator;
  identifying a target stimulation site after applying the mapping stimulation signal; and
  laparoscopically placing a stimulation electrode at the target stimulation site.

12. The method of claim 11 wherein the laparoscopically placing step is performed while visualizing with the endoscope.

13. The method of claim 11 wherein the laparoscopically placing step is performed by grabbing the stimulation electrode with an instrument associated with the endoscope.

14. The method of claim 11, wherein the endoscope is passed through the opening by grasping a distal end of the endoscope using a snare and pulling the endoscope through the opening and into the peritoneal cavity.

15. The method of claim 14, wherein the snare extends from the dilator.

* * * * *